United States Patent [19]

Langlois et al.

[11] 4,307,100
[45] Dec. 22, 1981

[54] NOR BIS-INDOLE COMPOUNDS USABLE AS MEDICAMENTS

[75] Inventors: Nicole Langlois; Yves Langlois, both of Bures S. Yvette; Ratremaniaina Z. Andriamialisoa, Les Ulis; Pierre Potieo, Bois d'Arcy; Pierre Mangeney, Paris, all of France

[73] Assignee: Agence Nationale de Valorisation de la Recherche (ANVAR), Paris, France

[21] Appl. No.: 67,439

[22] Filed: Aug. 20, 1979

[30] Foreign Application Priority Data

Aug. 24, 1978 [FR] France .................................. 78 24568
Aug. 24, 1978 [FR] France .................................. 78 24569
Feb. 6, 1979 [FR] France .................................. 79 02981

[51] Int. Cl.$^3$ .................. A61K 31/475; C07D 519/04
[52] U.S. Cl. ................................ 424/262; 260/244.4; 546/51
[58] Field of Search ...................... 260/244.4; 424/258, 424/262; 546/51

[56] References Cited

U.S. PATENT DOCUMENTS 4,144,237 3/1979 Kutney ..........................: 260/244.4

OTHER PUBLICATIONS

Mangeny, et al., J. Org. Chem., vol. 44, No. 22, pp. 3765–3769, 10/26/79.
Atta-ur-Rahman, Chemical Abstracts, vol. 77, 62204t (1972).
Kutney, et al., J. Am. Chem. Soc., vol. 90, No. 16, pp. 4504–4505 (1968).

Primary Examiner—Donald G. Daus
Assistant Examiner—Diana G. Rivers
Attorney, Agent, or Firm—Maky, Renner, Otto & Boisselle

[57] ABSTRACT

Compounds with antitumoral activity corresponding to the formula (I):

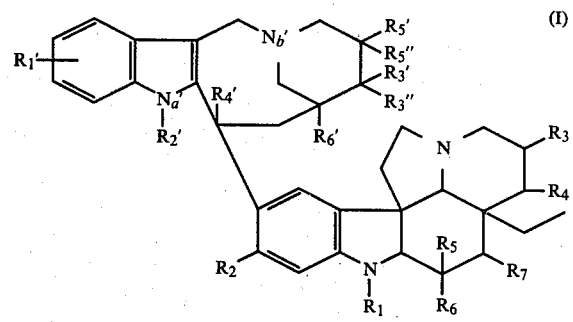

wherein $R'_1$ is a hydrogen atom or an alkoxy, acyl, formyl or haloacyl radical; $R'_2$ is a hydrogen atom or an alkyl radical; $R'_3$ and $R''_3$ are a hydrogen atom, hydroxyl radical or an alkanoyloxy radical, and together are a carbonyl group, and $R'_3$ and $R'_5$ together are an epoxy bridge or a double bond; $R'_4$ is a hydrogen atom or an alkyloxycarbonyl, hydroxymethyl, alkanoyloxymethyl or acetamido radical; $R'_5$ and $R''_5$ are a hydrogen atom or a hydroxyl, alkanoyloxyl, ethyl or 2-hydroxyethyl radical; $R'_6$ is a hydrogen atom or an ethyl, 2-hydroxyethyl or acetyl radical; $R_1$ is a hydrogen atom or an alkyl, formyl or acyl radical; $R_2$ is a hydrogen atom or alkoxy radical; $R_3$ is a hydrogen atom or a hydroxyl or alkanoyloxyl radical, and together with $R_4$ is an epoxy bridge or a double bond; $R_4$ is a hydrogen atom or a hydroxyl, alkanoyloxyl radical, and together with $R_5$ is an epoxy bridge; $R_6$ is an alkyloxycarbonyl, hydrazido, acetamido, hydroxymethyl or alkanoyloxymethyl radical; and $R_5$ and $R_7$ are a hydrogen atom or a hydroxyl and alkanoyloxyl radical; acid addition and quaternary ammonium salts thereof and 12-chloro derivatives thereof.

6 Claims, No Drawings

NOR BIS-INDOLE COMPOUNDS USABLE AS MEDICAMENTS

This invention relates to new bis-indole compounds, to a process for the preparation thereof and to the use threrof as medicaments.

It has been known for some time that natural alkaloids, such as vinblastine or vincristine, which correspond to the following formula:

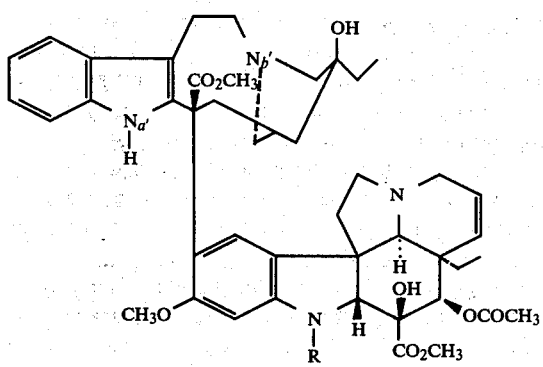

(vinblastine R represents $CH_3$; vincristine R represents CHO) and which may be isolated from several varieties of Catharanthus, more particularly from C. roseus, have anti-tumoral properties. In view of the fact that these alkaloids are only present in very small quantities in the plant, efforts have been made to prepare more active derivatives of these compounds, cf. Special Medicinal Patent Nos. 5487M and 6668M, French Patent No. 2,218,095. Processes for synthesising new compounds of identical structure, but differently substituted have also been proposed, cf. French Patent Nos. 74 43221 and 77 11081.

Nevertheless, throughout the prior art, the proposed compounds always retained the basic skeleton of vinblastine.

The present invention relates to new chemical compounds which show, in particular, anti-tumoral activity and which have a basic skeleton different from that of vinblastine.

The compounds according to the present invention correspond to the following formula:

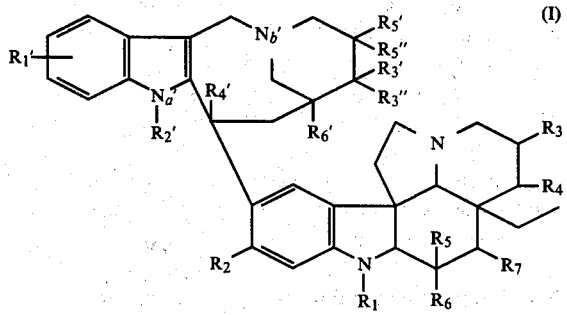

wherein
$R'_1$ represents a hydrogen atom or an alkoxy, acyl, formyl or haloacyl radical;
$R'_2$ represents a hydrogen atom or an alkyl radical;
$R'_3$ and $R''_3$ which may be the same or different each represents a hydrogen atom or a hydroxyl radical or an alkanoyloxyl radical or together represent a carbonyl group, or $R'_3$ and $R'_5$ together represent an epoxy bridge or a double bond;
$R'_4$ represent a hydrogen atom or an alkyloxycarbonyl, hydroxymethyl, alkanoyloxymethyl or acetamido radical;
$R'_5$ and $R''_5$ which may be the same or different each represents a hydrogen atom or a hydroxyl, alkanoyloxyl, ethyl or 2-hydroxyethyl radical;
$R'_6$ represents a hydrogen atom or an ethyl, 2-hydroxyethyl or acetyl radical;
$R_1$ represents a hydrogen atom or an alkyl, formyl, or acyl radical;
$R_2$ represents a hydrogen atom or an alkoxy radical;
$R_3$ represents a hydrogen atom or a hydroxyl or alkanoyloxyl radical, or $R_3$ and $R_4$ together represent an epoxy bridge or a double bond;
$R_4$ represents a hydrogen atom or a hydroxyl or alkanoyloxyl radical, or $R_4$ and $R_5$ together represent an epoxy bridge;
$R_6$ represents an alkyloxycarbonyl, hydrazido, acetamido, hydroxymethyl or alkanyloxymethyl radical; and
$R_5$ and $R_7$ represent a hydrogen atom or a hydroxyl or alkanoyloxyl radical.

The present invention also relates to the acid addition salts and quaternary ammonium salts of these compounds.

The alkyl radicals mentioned herein are preferably straight- or branched-chain lower alkyl radicals containing from 1 to 5 carbon atoms, such as methyl and ethyl radicals.

The alkoxy radicals mentioned herein are preferably lower alkoxy radicals corresponding to the above-mentioned alkyl radical, i.e. for example methoxy and ethoxy radicals.

The acyl radicals mentioned herein are, for example, the acyl radicals emanating from lower, saturated or unsaturated carboxylic acids, such as acetyl or propionyl radicals.

Similarly, the alkanoyloxy radicals are preferably radicals corresponding to the preceding acyl radicals, such as an acetyloxy radical.

The alkyloxycarbonyl radicals are preferably radicals in which the alkyl moiety corresponds to the preferred definition given above, for example a methoxycarbonyl radical.

Among the acid addition and quaternary ammonium salts, it is preferred to prepare the non-toxic, pharmaceutically acceptable salts, such as the salts of inorganic acids, such as hydrochloric acid, or ogranic acids, such as acetic acid, propionic acid, succinic acid or tartaric acid.

More particularly, the present invention relates to compounds corresponding to the following formula:

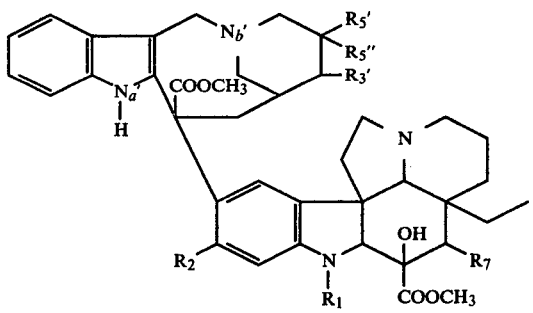

wherein
R'₃ represents a hydrogen atom or a hydroxy radical; and

R'₅ represents a hydrogen atom or a hydroxy radical; or

R'₃ and R'₅ together represent an epoxy bridge or a double bond;

R''₅ represents a hydrogen atom or an ethyl radical;

R₁ represents a hydrogen atom, an alkyl, formyl or acyl radical;

R₂ represents a hydrogen atom or a methoxy radical;

R₇ represents an alkanoyloxyl radical; (the dotted line represents a possible double bond); and to the corresponding salts.

In particular, the present invention relates to:
5'-noranhydrovinblastine,
5'-noranhydrovincristine,
5'-norleurosine,
12-chloro-5'-noranhydrovinblastine,
5'-nor-Na-desmethyl-Na-formyl leurosine.

The present invention also relates to a process for the preparation of the compounds corresponding to above formula (I) which is characterised in that:
(a) a compound corresponding to the following formula:

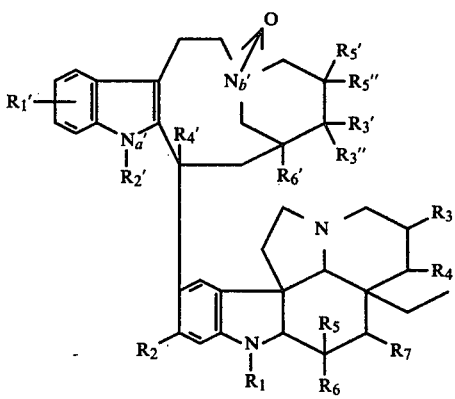

wherein the substituents are as defined above; is reacted in the presence of a reactant capable of forming immonium ions; and in that (b) the product obtained is treated with water and the compound corresponding to formula (I) is separated.

Among the immonium ion formers, it is preferred to use the halides, anhydrides or salts of organic or inorganic acids particularly optionally halogenated (preferably fluorinated) carboxylic acids.

The immonium ion formers used as, for example, acetic or trifluoroacetic acid anhydrides.

Step (a) is preferably carried out in an anhydrous organic solvent, such as a chlorinated solvent, methylene chlorine, dichloroethane or chloroform.

Reaction (a) is preferably carried out at a temperature of from −5° to +5° C., for example 0° C.

Step (b) is preferably carried out in one or more aqueous organic non-nucleophilic solvents. Preferred non-nucleophilic solvents are tetrahydrofuran and dioxzne. Step (b) may be carried out at ambient temperature.

Where the solvent used in step (a) is different from that used in step (b), the solvent has to be removed from the reaction mixture of step (a) before step (b) is carried out. For example, it may be distilled off.

It is also possible to carry out step (a) and step (b) in the same solvent, in which case step (a) is carried out in the anhydrous solvent to which water is added for carrying out step (b).

The compound corresponding to general formula (I) may be separated by known methods of separation. For example, it may be extracted using a chlorine-containing solvent, such as chloroform, and then separated from the chloroform phase by preparative chromatography.

Separation generally results in the formation of a secondary product which, by reduction, gives a compound corresponding to general formula (III) below, which may be recycled.

The compounds corresponding to general formula (II) are known (cf. the above-mentioned references) or may be obtained from compounds corresponding to the following formula (III):

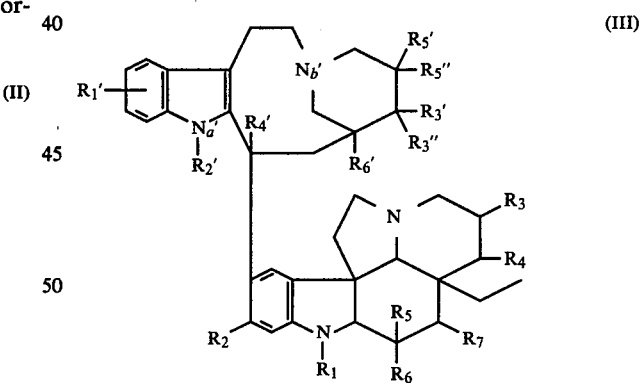

by known processes, in particular by oxidation, for example, using perbenzoic acids in a solvent, above all with m-chloroperbenzoic acid in chloroform or methylene chloride.

The present invention also relates to intermediate compounds which may be used in particular in the synthesis of chemical compounds corresponding to general formula (I) and which are obtained in step (a) of the process described above.

The intermediate compounds according to the present invention are the immonium ions corresponding to formula (V) below:

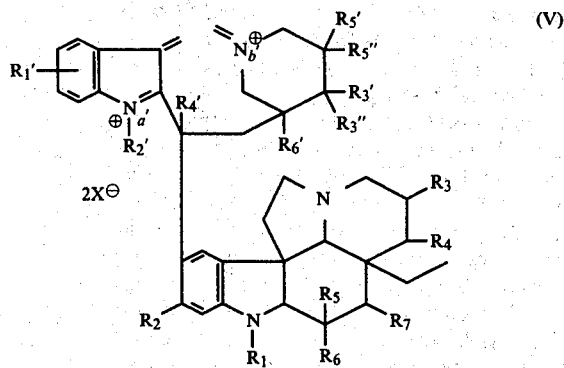

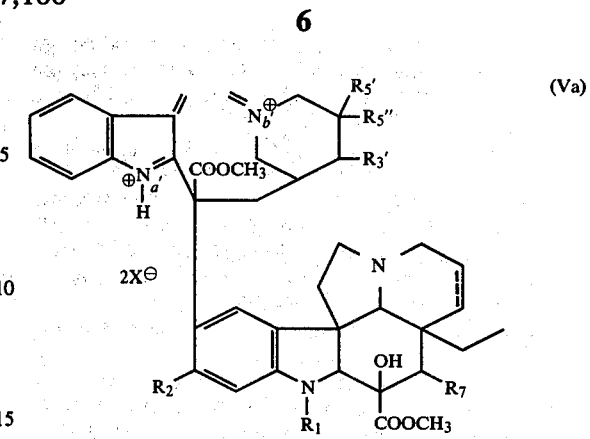

wherein the substituents are as defined above; and X⁻ represents the anion of an organic or inorganic acid.

Among the organic or inorganic acid anions represented by X⁻, particular references is made to the anions of halogenated, preferably fluorinated, carboxylic acids, such as trifluoro-acetic acid formula (V) represents the form in which the compounds are most readily used, but under certain pH conditions. The compounds corresponding to general formula (V) may be in the form of non-ionic compounds corresponding to formula (V') below:

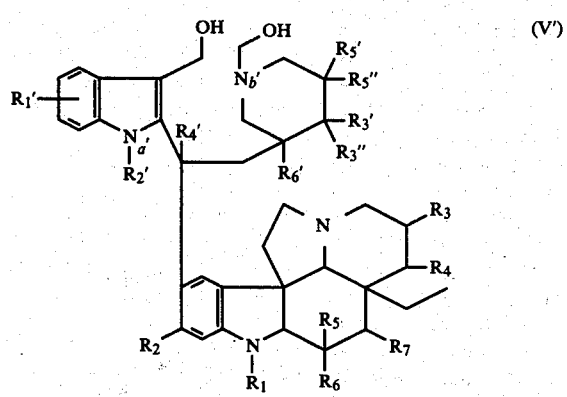

General formula (V) thus covers the compound corresponding to general formula (V) both in the form of immonium ions and in the non-ionic form, formula (V').

Among the particularly interesting compounds according to the present invention, reference is made to those in which the carbon atoms in the 16'-position, i.e. the carbon atom carrying the substituent R'₄, has the natural configuration, i.e. that of vinblastine or of vincristine which is the S configuration. It is one of the advantages of the present invention that the configuration of the carbon atom in the 16'-position is retained.

More particularly, the present invention relates to compounds corresponding to the following formula (Va):

wherein
- R'₃ represents a hydrogen atom or a hydroxy radical; and
- R'₅ represents a hydrogen atom or a hydroxy radical; or
- R'₃ and R'₅ together represent an epoxy bridge or a double bond;
- R"₅ represents a hydrogen atom or an ethyl radical;
- R₁ represents a hydrogen atom, an alkyl, formyl or acyl radical;
- R₂ represents a hydrogen atom or a methoxy radical;
- R₇ represents an alkanoyloxy radical; (the dotted line represents a possible double bond); and
- X⁻ is as defined above.

The intermediate compounds corresponding to general formula (V) are obtained in step (a) of the process described above.

The present invention also relates to another process for preparing the compounds corresponding to general formula (I) in which a compound corresponding to the following formula (IV):

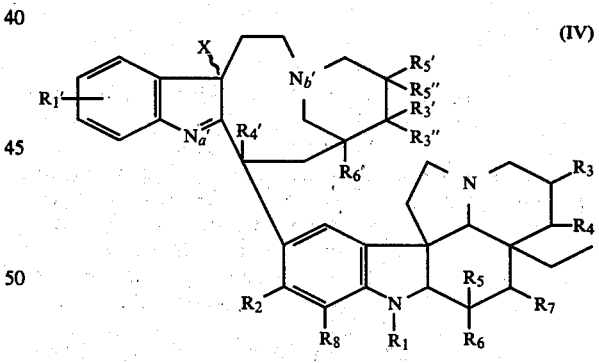

wherein the substituents are as defined above; and X represents a halogen atom, a hydroxy, hydroperoxy or alkanoyloxy radical; is treated with a mixture of water and at least one organic solvent.

The halogens which may substitute the compounds in question are fluorine, chlorine, bromine and iodine, generally chlorine.

The process according to the present invention may be carried out without a catalyst, although the reaction may be catalysed by Ag⁺ ions emanating from silver salts, such as silver perchlorate, tetrafluoroborate, trifluoroacetate and acetate, or even by an acid reactant, for example an inorganic acid, such as hydrochloric acid.

Various organic solvents may be used and, although it is advantageously miscible with water, it may be immiscible without the reaction being affected by the presence of two phases.

Suitable solvents are in particular ethers, such as tetrahydrofuran and dioxane and mixtures thereof.

The ratio of water to organic solvent in the mixture is not critical, although it is preferred to use a mixture having a ratio, by volume, of from 30:70 to 70:30, preferably 50:50. However, much lower contents of water or organic solvent are also possible.

The reaction temperature is preferably from 0° to 70° C.

The reaction pressure is not a critical parameter, although the reaction is preferably carried out under an inert atmosphere, for example of argon or nitrogen.

On completion of the reaction, the compound corresponding to general formula (I) may be extracted by known methods although it is of particular advantage to extract it using a chlorine-containing organic solvent, such as chloroform.

The thus-obtained organic phase may be evaporated in vacuo and purified, for example, by chromatography.

The compounds corresponding to general formula (IV) may be obtained from compounds corresponding to the following general formula (III):

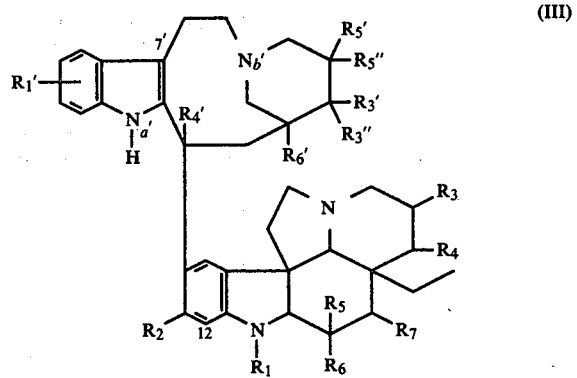

which are known compounds or which may be prepared, in particular, by the processes described in French Pat. Nos. 74 43221 and 77 11081.

Thus, to prepare the compounds corresponding to general formula (IV) wherein X represents a halogen atom; a compound corresponding to general formula (III) is halogenated using a reactant capable of forming a positive halogen ion in an organic solvent, such as benzene, chloroform, dichloromethane, acetonitrile, tetrahydrofuran or dioxane.

The agents capable of forming a positive halogen ion may be N-halobenzotriazoles, such as N-chlorobenzotriazole, a hypohalite, such as t-butyl hypochlorite or sodium hypochlorite, an N-haloamide, such as N-chloroacetamide and N-bromoacetamide, or an N-haloimide, such as N-chlorosuccinimide or N-bromosuccinimide.

This reaction is preferably carried out at a temperature of from −10° to +20° C. in particular at 0° C., under an inert atmosphere, although this is not an essential requirement.

If the reaction is carried out using substantially stoichiometric proportions of reactant, the corresponding 7' haloindolenines are almost exclusively obtained. However, if the reactant capable of forming a positive halogen ion is used in twice the stoichiometric quantity, the corresponding 12,7'-dihaloindolenines are obtained and, through the subsequent reaction, give the 12-halo derivative corresponding to general formula (I).

If desired, the compounds corresponding to general formula (IV) may be isolated from the halogenation reaction mixture by known methods, in particular by extraction using a chlorine-containing solvent, such as chloroform. The thus-obtained phase may be purified, for example by evaporation in vacuo and chromatography. If it is desired to isolate the compounds corresponding to general formula (IV), it is obviously necessary in the light of the foregoing to work in anhydrous medium. However, it is generally not necessary to isolate the compound corresponding to general formula (IV) which may be directly used in its reaction medium for the preparation of the compound corresponding to general formula (I).

It is also possible directly to prepare the compound corresponding to general formula (I) by combining the formation of the compound corresponding to general formula (IV) and the formation of the compound corresponding to general formula (I) by reacting the compound corresponding to general formula (III) with the reactant capable of forming a positive halogen ion in a water-containing organic solvent, in which case the compound corresponding to general formula (IV) only appears transiently.

In this latter case, it would also be possible to add $Ag^+$ ions or an acid reagent to the mixture in order to accelerate the reaction by which the compound corresponding to general formula (I) is formed.

Compounds corresponding to general formula (IV) wherein X represents a hydroperoxide radical, may be prepared by the action of oxygen on compounds corresponding to general formula (III) in the presence of a metal salt, for example.

Compounds corresponding to general formula (IV) wherein X represents a hydroxy radical, may be prepared from compounds wherein X represents a hydroperoxide radical, by reduction using a trialkyl or triaryl phosphite, such as triethyl phosphite.

Compounds wherein X represents an alkanyloxy radical, may be prepared by reacting a lead tetracarboxylate, such as lead tetraacetate, with compounds corresponding to general formula (III).

The present invention also relates to the 7'-haloindolenines corresponding to general formula (IV) and the 12-chloro derivatives corresponding to general formula (I), which show anti-tumoral properties, as new industrial compounds which may be used, in particular, as synthesis intermediates in the process according to the present invention.

The present invention is illustrated by the following Examples.

EXAMPLE (Scheme I) 1:

(a) Preparation of the Nb' oxide or $\Delta^{15'}$ deshydroxy-20' vincaleucoblastine (II')

180 mg (1.04 mmole) of m-chloroperbenzoic acid are added all at once with stirring under argon at 0° C. to a solution of $\Delta^{15'}$ deshydroxy-20' vincaleucoblastine (III') (748 mg; 0.94 mmole) in 10 ml. of methylene chloride. After standing for 30 minutes at 0° C. the reaction medium is taken up with 100 ml. of chloroform and the organic phase is washed 4 times with 3 ml. of an aqueous solution of sodium bicarbonate (40 g/l). The organic phase is then washed until neutral with water saturated with sodium chloride (3 times 10 ml) dried over sodium sulphate, filtered and evaporated in vacuo to give 712 mg of the Nb' oxide of $\Delta^{15'}$ deshydroxy-20' vincaleucoblastine (yield 93%). U.V. ($\lambda$nm, $\epsilon$): 213, 268, 289, 293, 310. N,R$^1$H (400 MHz; $\delta$=O0PM. TMS; J: Hz) 9.50 (s, 1H) $C_{16}$—OH; 8.19 (s 1H) Na'—H; 7.70 (d, 1H, J$\simeq$7.5)$C_9$, H or $C_{12}$ H; 7.19 and 7.14$C_{10}$, H and $C_{11}$, H; 7.07 (d, J$\simeq$7.5) $C_{12}$, H or $C_9$, H; 6.43 (s, 1H)$C_9$H; 6,11 (s 1H)$C_{12}$H; 5.84 (dd, 1H, $J_{14,15} \simeq$10 Hz and $J_{3,14}\simeq$4.5$C_{14}$H; 5.44 (1H)$C_{15}$, H, 5.41 (s 1H)$C_7$-H; 5.27 (d, 1H, $J_{14,15} \simeq$10 Hz)$C_{15}$H; 4.51 (m, 2H) 4.32 (d, 1H) and 3.98 (d, 1H): Nb'CH; 3.84 (s 3H), 3.78 (s 3H) and 3.69 (s 3H)$C_{11}$OCH$_3$, $C_{16}$CO$_2$CH$_3$ and $C_{16}$, CO$_2$CH$_3$ 2.62 (s 3H)NaCH$_3$; 2.09 (s 3H) OCOCH$_3$; 1.06 (t, 3H, $J_{18', 19'}$: 7 Hz) $C_{18}$, H and 0.64 (t,3H, $J_{18,19}\simeq$7 $C_{18}$H-S.M.: 808, 806, 792 (M-16) 777, 871, 733, 669, 633, 631, 612, 611, 610, 510, 469, 282, 222, 200, 193, 144, 136, 135, 122, 121 (base peak) 108, 107.

(b) Preparation of 6'-nor $\Delta^{15'}$ deshydroxy-20' vincaleucoblastine (I')

276 $\mu$l of trifluoroacetic anhydride (189 mmole) are added with stirring under argon at 0° C. to a solution of the preceding Nb' oxide (345 mg; 0.43 mmole) in 2 ml. of dry methylene chloride. After standing for 2 hours at 0° C. the reaction medium is evaporated to dryness using an electric pump and taken up with 8 ml of tetrahydrofuran and 30 ml of water, stirred for 1 hour at ambient temperature, taken up with 50 ml of chloroform and washed with a saturated aqueous solution of sodium chloride. The organic phase is then dried and evaporated. The thus-obtained crude product is purified by chromatography on a thick layer of silica (eluent CHCl$_3$/MeOH 90:10). The least polar product (90 mg: 27%) corresponds to the compound (I'). [$\alpha$]=+52.4 (c=3.24) CHCl$_3$, U.V. ($\lambda$nme): 215 (36700), 268 (11000), 282 (9500), 293 (7600), 310 (4400).

D.C. ($\lambda$nm, $\Delta\epsilon$): 312 (+3.4), 305(+3.02), 258 (+13.3), 230 (+31.6), 210 (-44.3).

NMR$^1$H (400 MHz; $\delta$=OPPM. TMS; J: Hz) 8.50 (s 1H) OH or NH: 77.7 (d, 1H, J=8) NH or aromatic; 7.15 (m, 4H) aromatic; 6.34 (s 1H)$C_9$H; 6.08 (s 1H)$C_{12}$-H; 5.83 (dd, 1H, J=3.5 and 9.5) $C_{14}$H; 5.76 (m, 1H)$C_{15'}$-H; 5.37 (s 1H)$C_{17}$H: 5.25 (d, 1H, J=9.5) $C_{15}$H; 4.58 (m, 1H) and 4.41 (d, 1H)$C_6'$H and $C_6'$H'; 3.83 (s 3H); 3.13 (s 3H); 3.68 (s 4H) $C_{16}$CO$_2$CH$_3$, $C_{11}$OCH$_3$, $C_{16'}$CO$_2$CH$_3$ and $C_{21}$H; 2.69 (s 3H) Na-CH$_3$; 2.57 (s 1H), $C_2$H; 2.06 (s 3H) OCOCH$_3$; 1.07 (t, 3H j=7); 0.70 (t, 3H), J =7) $C_{15'}$H and $C_{18}$H. S.M. 794, 792, 748, 656, 598, 522, 480, 450, 436, 331, 282, 240, 222, 210, 165, 152, 144, 136, 135, 122. I.R. ($\nu$ cm$^{-1}$): 1740, 3420.

The most polar product (275 mg) taken up with MeOH (3 ml), reduced using an excess of sodium borohydride, extracted and purified in the same as described above gives 200 mg of $\Delta^{15'}$ deshydroxy-20' vincaleucoblastine (III') which may be recycled.

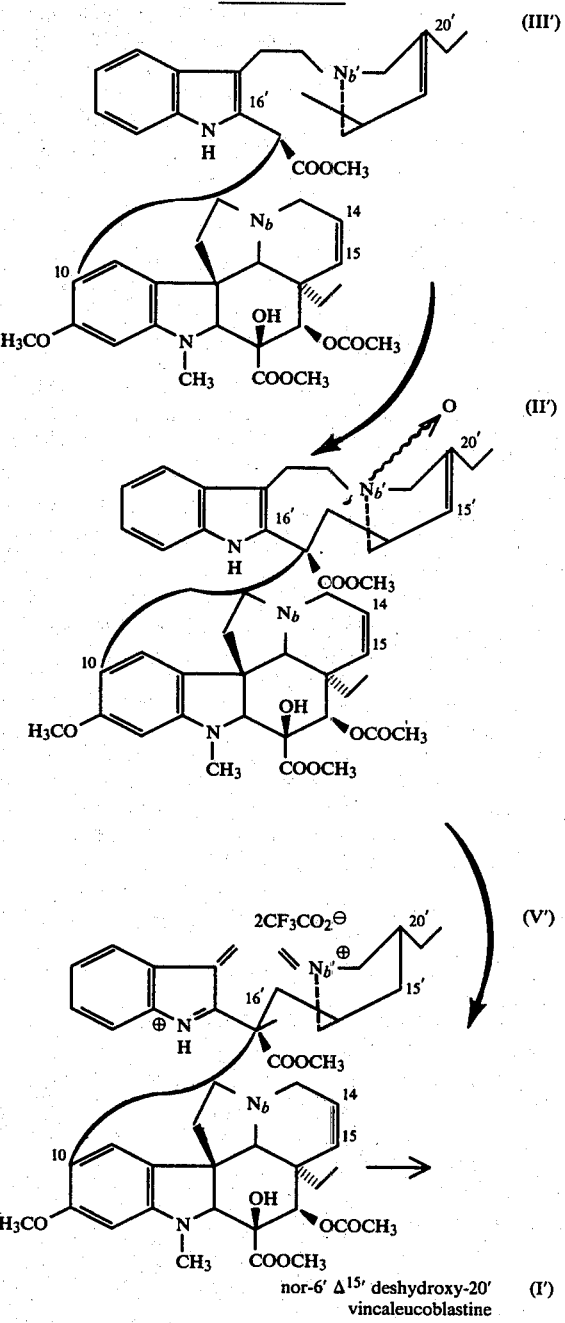

SCHEME I nor-6' $\Delta^{15'}$ deshydroxy-20' vincaleucoblastine (I')

EXAMPLE 2

(a) Preparation of the 7'-chloroindolenine of anhydrovinblastine (formula (IV')

A solution of 76 mg of N-chlorobenzotriazole (0.49 mM) in 20 cc. of anhydrous methylene chloride is added with stirring at 0° C. to a solution of 330 mg of anhydrovinblastine (formula (III') (0.42 mM) in 10 cc of the same solvent maintained under an argon atmosphere. After 10 minutes, the solvent is removed under reduced pressure at low temperature (below 15° C.). The 7'chloroindolenine of the anhydrovinblastine (72 mg, yield 21%) is separated by chromatography on a layer of silica (eluent: CHCl$_3$—MeOH 95:5) from the starting anhydrovinblastine (140 mg, 42%) which may be recycled, and the other secondary products.

The 7'-chloroindolenine has the following characteristics: IR (CHCl$_3$): 3640, 2920, 1745, 1620, 1505, 1465, 1435 cm$^{-1}$. UV (EtOH) λ max (ε): 215 (61000); 255 (21000); 313 nm (12250) (EtOH+H$^+$) λ max: 216, 260, 302 nm: indolenine dihydroindole. DC (EtOH) λ nm (Δε): 215 (−70): 230 (+35.8); 258 (−2.0); 285 (+6.9): 311 (−5.1); 345 (+14.1). SM peaks at m/e: 792, 748, 703, 691, 612, 598 (100%) 538, 522, 480, 450, 331, 329, 282, 222, 200, 165, 152, 144, 136, 135, 122, 121, 107.

NMR$^1$H (CDCl$_3$, δ=0 ppm TMS, 240 MHz): 7.58 (wide s, 1H, attributed to C$_9$—H); 7.3-7.1 (aromatics); 5.91 (s, 1H, C$_{12}$—H); 5.80 (dd, 1H, J$_{14,15}$=9 and J$_{3,14}$=3 Hz C$_{14}$—H) 5.43 (s,1H, C$_{17}$—H); 5.24 (m, 1H, C$_{15}$,—H); 5.05 (d, 1H, J∼9 Hz, C$_{15}$—H); 3.78-3.71 and 3.52 (3s, 9H, C$_{11}$—OCH$_3$, C$_{16}$—CO$_2$CH$_3$ and C$_{16}$,—CO$_2$CH$_3$); 2.62 (s, 3H, N$_a$—CH$_3$); 2.03 (s, 3H, COCH$_3$); 1.00 (t, 3H, J∼7.5 Hz attributed to C$_{18}$,—H) and −0.28 (attributed to C$_{18}$—H).

(b) Preparation of 5'-noranhydrovinblastine (formula (I') from the 7'-chloroindolenine of anhydrovinblastine:

A solution of 9.0 mg of AgBF$_4$ (0.046 mM) in 7 cc of a mixture of THF and H$_2$O (50:50 by volume) is added to 33 mg of the 7'-chloroindolenine obtained in stage (a) maintained under an argon atmosphere. The mixture is stirred for 4 hours at 50° C., cooled, concentrated under reduced pressure at from 25° to 30° C. diluted with 10 cc of an aqueous Na$_2$CO$_3$ solution (10%) and extracted with chloroform. The organic phases are dried over Na$_2$SO$_4$ and filtered. Removal of the solvent under reduced pressure gives quantitatively 30 mg of 5'-noranhydrovinblastine identical with a sample prepared by the process described in Example 1.

Scheme II below describes the preparation of this compound by the process according to the present invention.

EXAMPLE 3

(a) Preparation of the 12,7'-dichloroindolenine of anhydrovinblastine

A solution of 10.7 mg of N-chlorobenzotriazole (0.07 mM) in 1.5 cc of methylene chloride and then 11.3 mg of the same reactant are added at 0° C. to a solution of 50 mg of anhydrovinblastine (0.063 mM) in 1.7 cc of anhydrous methylene chloride maintained under an argon atmosphere. After stirring for 45 minutes, the reaction medium is treated in the same way as described in Example 1(a). After purification by chromatography on a layer of silica (eluent: CHCl$_3$/MeOH 93:7), the 12,7'-dichloroindolenine of anhydrovinblastine is obtained in a yield of the order of 45% and has the following characteristics: IR (CHCl$_3$): 3840, 2920, 1750, 1615, 1465, cm$^{-1}$. UV (EtOH)λ max (ε): 223 (35500); 255 (10700); 310 nm (7200) (EtOH+H$^+$)λ max: 226, 262, 305 nm: indolenine dihydroindole. DC (EtOH)λ max (Δε): 233 (+11.5); 259 (−2.2); 300 (+4.5) 325 (+5.1). SM peaks at m/e: 826, 782, 752, 737, 632, 591, 572, 556, 514, 484, 365, 282, 222, 182, 167, 152, 144, 136, 135 (100%), 122, 121, 120, 107, 106. NMR$^1$H (CDCl$_3$): 7.53 (1h, attributed to C$_9$—H); 7.34 and 7.25 (aromatics) 5.77 (dd, 1H, J$_{14,15}$)=10 and J$_{3,14}$32 4 Hz C$_{14}$—H); 5.41 (s, 1H, C$_{17}$—H); 5.29 (m, 1H, C$_{15}$—H); 5.08 (d, 1H, J$_{14,15}$)=10 Hz, C$_{15}$—H); 3.94, 3.78 and 3.53 (3 s, 9H, C$_{11}$—OCH$_3$, C$_{16}$—CO$_2$CH$_3$ and C$_{16}$'—CO$_2$CH$_3$); 2.86 (s, 3H, N$_a$CH$_3$); 2.03 (s, 3H, COCH$_3$); 1.01 (t, 3H, J=7 Hz, attributed to C$_{18}$'—H) and −0.17 ppm (attributed to C$_{18}$—H).

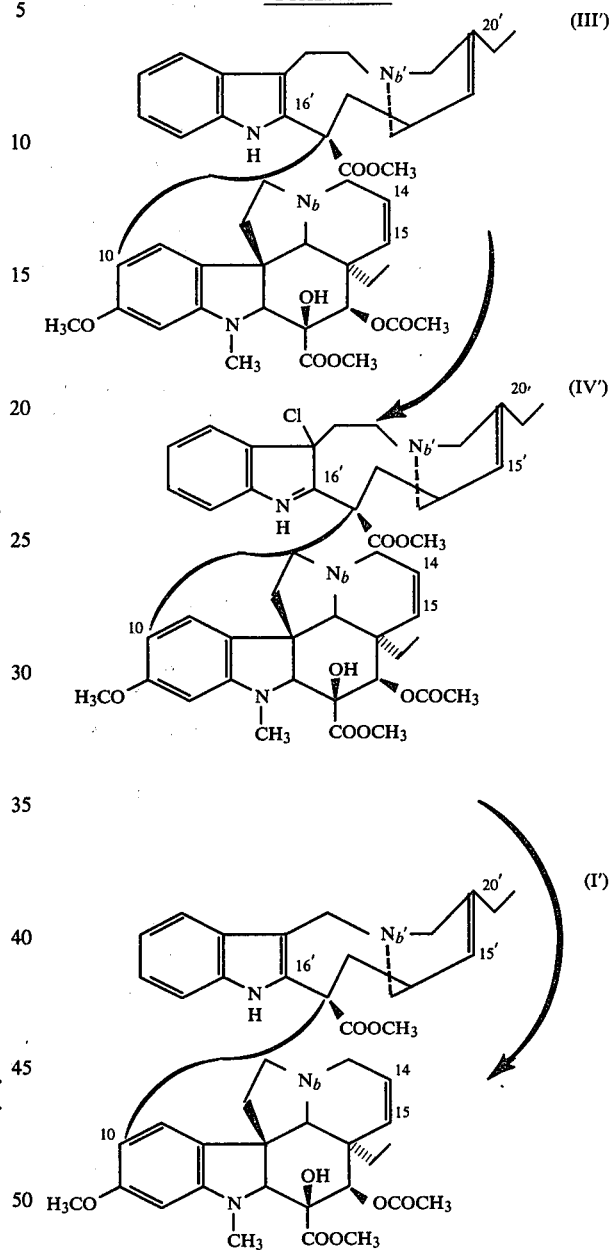

SCHEME II (b) Preparation of 12-chloro-5'-noranhydrovinblastine

A solution of 6 mg of AgBF$_4$ (3×10$^{-5}$ M) in 2.8 cc of a mixture of THF and H$_2$O (50:50 by volume) is added under argon at 0° C. to a solution of 22 mg of 12-chloro-7'-chloroindolenine (2.5×10$^{-5}$ M) obtained in stage (a) in 1.2 cc of the same mixture. The reaction mixture is stirred for 17 hours at from 40° to 45° C. and then treated in the same way as in Example 1(b) to obtain 19.6 mg of 12-chloro-5'-noranhydrovinblastine (yield 95%) having the following characteristics: [α]$_D^{15}$+22° (CHCl$_3$, C=0.59)

IR (CHCl$_3$): 3480, 3460, 2920, 1750, 1610, 1462 cm$^{-1}$
UV (EtOH)λ max (ε): 221 (46000); 272 (17000); 293 (10500) and 308 nm (4000).

DC (EtOH)λ max (Δε): 216 (−46.2); 231 (+29.1); 245 (+11.5); 262 (+25.7); 293 (−1.1); 306 (+3.4); 320 (3.4) SM peak at m/e: 828, 826, 782, 768, 725, 646, 632, 565, 282, 222, 152, 144, 136 (100%) 135, 123, 122, 121, 107. NMR$^1$H (CDCl$_3$); 8.47 (s, 1H, N$_{a'}$—H); 7.69 (1H, arom. indole); 7.14 (3H, arom. indoles); 6.36 (s, 1H, C$_9$—H); 5.89 (dd, 1H, J$_{14,15}$=10 and J$_{3,14}$~4 Hz, C$_{14}$—H); 5.70 (1H, C$_{15}$,—H): 5.29 (s, 1H, C$_{17}$—H); 5.27 (1H, C$_{15}$—H); 4.28 (dd, 2H, J$_{6a,6b}$=14 Hz, C$_{6'}$—H); 3.95, 3.78 and 3.75 (3 s, 9H, C$_{11}$—OCH$_3$, C$_{16}$—CO$_2$CH$_3$ and C$_{16'}$—CO$_2$CH$_3$); 3.70 (s attributed to C$_2$—H); 2.97 (s, 3H, N$_a$—CH$_3$); 2.09 (s, 3H, COCH$_3$); 1.06 (t,3H, J$_{18',19'}$=6.5 Hz, C$_{18'}$,—H) and 0.70 ppm (t, 3H, J$_{18',19}$=6 Hz, C$_{18}$—H).

EXAMPLE 4

(a) Preparation of the 7'-chloroindolenine of anhydrovincristine 29 mg of N-chlorobenzotriazole (0.19 M) are added with stirring to a solution of 120 mg of anhydrovincristine (0.15 mM) prepared as described (J. P. Kutney, J. Balsevitch, T. Honda, P. H. Liao, H. P. M. Thillied and B. R. Worth, Can J. of Chem. (1978), 56, pages 3560) in 12 cc. of anhydrous methylene chloride maintained under argon at a temperature of 0° C. After stirring for 2 hours 30 minutes, the reaction mixture is evaporated to dryness under reduced pressure at a temperature below 20° C. The unreacted anhydrovincristine (20 mg, 17%) is separated by chromatography on a layer of silica (eluent: AcOEt/MeOH 90:10) from the 7'-chloroindolenine of anhydrovincristine (87 mg, yield 70%) which has the following characteristics:

IR: 3000, 1760, 1680, 1615, 1600 cm$^{-1}$.

UV (EtOH)λ max: 222, 256, 310 nm (EtOH+H$^-$)λ max: 225, 254, 296 nm.

DC (EtOH) nm: 235 (+); 300 (−); 320 (+). (EtOH+H$^+$)λ nm: 225(+); 260 (+) 305 (+).

SM: 806, 804, 773, 762, 645, 612, 610, 552, 536, 494, 466, 401, 366, 358, 329, 282, 136 (100%) 135, 122, 121.

(b) 5'-noranhydrovincristine 20 mg of AgBF$_4$ (0.1 mM) are added with stirring at ambient temperature to a solution of 60 mg of anhydrovincristine-7'-chloroindolenine (0.07 mM) in 3 cc of a mixture of THF and water (50:50) by volume). The mixture is stirred for 2 hours 30 minutes at 45° C. and then extracted using chloroform in the presence of a *10% aqueous solution of Na$_2$CO$_3$. After washing with water, drying over Na$_2$SO$_4$ and evaporation of the solvent under reduced pressure, 5'-noranhydrovincristine is isolated in a yield of 51 mg (90%). It has the following characteristics:

IR (CHCl$_3$): 3400, 2950, 1745, 1680 cm$^{-1}$.

UV (EtOH): 215, 259, 282, 292 nm

DC (EtOH)λ nm: 205(−); 220(+); 250 (+); 295 (+)

SM peaks at m/e: 806, 794, 792, 776, 762, 645, 630 610, 599, 587, 536, 508, 494, 466, 152, 136 (100%) 135, 122, 121, NMR$^1$H (CDCl$_3$): 8.76 (s, 1H, OH); 8.48 (wide s, 1H, N$_{a'}$—H): 8.18 (0.5H) and 7.73 (1.5H) N$_a$—CHO+aromatic; 7.18 3H, aromatics); 6.80 (s, 1H, C$_9$—H); 6.71 (2s, 1H, C$_{12}$—H); 5.91 (m, 1H, C$_{14}$—H); 5.70 (m, 1H, C$_{15'}$—H); 5.40 (d, 1H, J$_{14,15}$=10 Hz, C$_{15}$—H); 5.20 (2s, 1H, C$_{17}$—H); 4.75 and 4.50 (2s, 1H, C$_2$—H); 3.91, 3.75 and 3.71 (3s, 9H, C$_{11}$—OCH$_3$, C$_{16}$—CO$_2$CH$_3$ and C$_{16'}$—CO$_2$CH$_3$); 2.09 (2s, 3H, COCH$_3$); 1.08 (t, 3H, J=7 Hz) and 0.71 ppm (3H), C$_{18'}$—H) and C$_{18}$—H).

EXAMPLE 5

(a) Leurosine-7'-chloroindolenine 23 mg of N-chlorobenzotriazole (0.15 nM) are added to a solution of 100 mg of leurosine (0.124 mM) in 10 cc of anhydrous methylene chloride maintained under argon at a temperature of 0° C. After stirring for 1 hour 45 minutes at 0° C. and evaporation of the solvent under reduced pressure at a temperature below 20° C. the products are separated by chromatography on silica (eluent: AcOEt/EtOH 3:1). Leurosine-7'-chloroindolenine is thus isolated in a yield of 62 mg (57%) together with 30 mg of leurosine which may be recycled.

The leurosine-7'-chlorinolenine has the following characteristics:

IR (CHCl$_3$): 3000, 1750 cm$^{-1}$

UV (EtOH)λ max: 200, 248, 300 nm.

DC (EtOH)λ nm: 245 (+), 295(−), 325(+)

EtOH+H$^+$)λ nm: 210(−) 225 (+), 270(−), 295(+)

SM peaks at m/e: 844, 843, 842, 841, 807, 684, 682, 670, 648, 602, 494, 352, (100%), 310, 308, 283, 154, 135, 122, 121.

(b) 5'-norleurosine 10 mg of AgBF$_4$ are added to a solution of 40 mg of leurosine-7'-chloroindolenine (40 mg, 4.75.10$^{-5}$ M) in 4 cc of a mixture of THF and H$_2$O (50:50) by volume) and the mixture is stirred for 3 hours at 50° C. After extraction as in Example 3(b). 5'-norleurosine identical with a sample prepared by a process similar to the process described in Example 1 is obtained in a yield of 35 mg (93%) and has the following characteristics:

IR (CHCl$_3$) 3350, 2950,1750 cm$^{-1}$ (C=0.5 CHCl$_3$) [α]$_D^{20°}$=32° UV (EtOH)λ max: 217, 270, 285 (ep.) 293 (ep) 211 nm DC (EtOH)λ nm: 215(−), 220(+), 255(+), 280(−), 310(+). SM peaks at m/e, 810, 796, 794, 761, 750, 656, 649, 637, 633, 598, (100%) 538, 522, 496, 480, 469, 450, 449, 448, 369, 367, 340, 331, 329, 282, 240, 238, 222, 210, 208, 188, 174, 165, 154, 152, 135, 122, 121, 107.

NMR$^1$H (CDCl$_3$): 8.31 (s, 1H, NaH): 7.55 (1H, aromatic); 7.06 (3H aromatics); 6.30 (s, 1H, C$_9$—H) 6.00 (s, 1H C$_{12}$—H); 5.76 (dd, 1H J$_{14,15}$=10 and J$_{3,14}$)=4 Hz, C$_{14}$—H); 5.31 (s, 1H, C$_{17}$—H); 5.23 (d, 1H, J$_{14,15}$=10, C$_{15}$—H); 4.30 4.11 (2d, J$_{6'a,6'b}$=13 Hz, C$_{6'}$—H); 3.76, 3.73 and 3.66 (3s, 9H, C$_{11}$—OCH$_3$, C$_{16}$—CO$_2$CH$_3$ and C$_{16'}$—CO$_2$CH$_3$); 2.66 (s, 3H, N$_a$—CH$_3$); 2.05 (s, 3H, COCH$_3$); 1.05 and 0.66 ppm (2t, 6H, J=7 Hz, C$_{18}$—H and C$_{18'}$—H).

EXAMPLE 6

Preparation of the 7'-chloroindolenine of N$_a$-desmethyl N$_a$-formyl leurosine 14 mg of N-chlorobenzotriazole (0.092 nM) are added with stirring to a solution of 60 mg of N$_a$-desmethyl N$_a$-formyl leurosine or leuformine (0.072 mM) in 6 cc of anhydrous methylene chloride maintained under argon at a temperature of 0° C. After stirring for 2 hours, the reaction mixture is evaporated to dryness under reduced pressure at a temperature below 20° C. After the addition of 1.5 cc of methanol and 10 cc of an aqueous sodium carbonate solution (40%) the product is extracted with benzene. After washing with water, drying over Na$_2$SO$_4$, evaporation of the solvent under reduced pressure and purification by chromatography on a layer of silica (eluent:CHCl$_3$/CH$_3$OH 95:5) saturated with NH$_3$), the 7'-chloroindolenine of N$_a$-desmethyl N$_a$-formyl leurosine is obtained in a yeild of 52 mg (85%) and has the following characteristics:

IR (CHCl$_3$); 3000, 1760, 1690, 1600 cm$^{-1}$.
UV (EtOH)λ max: 226, 256, 310 nm.
EtOH+OH+)λ max: 225, 254, 298 nm.
DC (EtOH)λ nm: 205 (−) 235 (+); 258 (+) 295 (−) 325 (+). EtOH+H+)λ nm: 230 (+); 255(+); 295 (+).
SM: 836, 822, 616, 365, 282, 149, 133, 122 (100%) 121.

5′-nor-N$_a$-desmethyl N$_a$-formyl leurosine 20 mg of AgBF$_4$ (0.1 mM) are added with stirring at ambient temperature to a solution of 50 mg of N$_a$-desmethyl N$_a$-formyl leurosine 7′-chloroindolenine (0.07 mM) in 4 cc of a mixture of THF and H$_2$O (50:50) by volume). The mixture is stirred for 16 hours at 20° C. and then extracted with ether in the presence of 10% Na$_2$CO$_3$. After drying over Na$_2$SO$_4$, evaporation of the solvent under reduced pressure and purification by chromatography on a layer of silica (eluent: CHCl$_3$/CH$_3$OH 95:5, cell saturated with NH$_3$) 5′-nor-Na-desmethyl Na-formyl leurosine is isolated in a yield of 20 mg (40%) and has the following characteristics:

IR (CHCl$_3$): 3400, 2950, 1750, 1680 cm$^{-1}$.
UV (EtOH)λ max: 222, 260, 286, 295 nm.
DC (EtOH)λ: 205, (−); 225 (+); 225 (+); 298 (+).
SM peaks at m/e: 824, 822, 764, 612, 610, 584, 494, 282, 154, 152, 144, 136 (100%) 122, 121. NMR$^1$H (CDCl$_3$): 8.70 (s, 1H, OH) 8.41 (s, side, 1H, N$_{a'}$—H); 8.12 (0.5H) and 7.70 (0.5H); NaCHO: 7.62 (d, J=7 Hz 1H, aromatic); 7.12 (m, 3H aromatics) 6.76 (s, 1H, C$_9$—H); 6.64 (2s, 1H, C$_{12}$—H) 5.86 (dd, J$_{14,15}$=10 Hz J$_{3,14}$=3 Hz, 1H, C$_{14}$—H); 5.33 (d, J$_{14,15}$=10, 1H, C$_{15}$—H), 5.16 (2s, 1H, C$_{17}$—H); 4.70 and 4.45 (2s, 1H, C$_2$—H); 4.32 (d, J$_{AB}$=12 Hz, 1H, C$_6$'H′); 3.92; 3.76 and 3.68 (3s, 9H) C$_{11}$OCH$_3$, C$_{16}$CO$_2$CH$_3$, C$_{16'}$CO$_2$CH$_3$); 2.05 (2s, 3H, OCOCH$_3$); 1.07 (t, J$_{18,19}$=7 Hz, 3H) and 0.70 (t, J$_{18,19}$=7 Hz, 3H) C$_{18}$—H) and C$_{18'}$—H).

The compounds corresponding to general formula (I) according to the present invention show anti-tumoral properties and may therefore be used in the treatment of various tumoral diseases, such as leukaemia.

Accordingly, the present invention also relates to the compounds corresponding to general formula (I) and to the pharmaceutical compositions containing them as new medicaments.

The results of in vitro and in vivo pharmacological studies conducted on the compounds of the preceding Examples are given in the following:

(1) Inhibition of the polymerisation of tubulin

The receiver of anti-tumoral indolic alkaloids of the vinblastine type is tubulin.

It is readily extracted from pigs' brains where it preresents 10% of the soluble proteins.

The polymerisation of tubulin into microtubules may readily be followed by means of a UV spectrophotometer observing at 350 nm. The maximum polymerisation velocity is thus determined; it is reduced by the addition of inhibitors of the vinblastine type and a concentration, I$_{50}$, reducing the polymerisation velocity by half is obtained for each substance tested. A second effect of these products is taken into consideration: with higher doses, after complete inhibition of polymerisation, spiralisation of the tubulin is observed (verified by electron microscopy) and a new concentration, S$_{50}$, corresponding to the appearance of 50% of the phenomenon is determined.

The results of each product are always compared with those of the vinblastine used as reference.

TABLE I

The results of the interaction tests with tubulin carried out on the tartrates are summarised in the following Table (tubulin concentration ~ 2 mg/ml):

| Compound | I$_{50}$/I$_{50}$ vinblastine (a) | S$_{50}$/S$_{50}$ vinblastine (b) |
|---|---|---|
| 5′-noranhydrovinblastine | 0.7 | 0.8–1.0 |
| 12-chloro-5′-noranhydrovinblastine | 13 | |
| anhydrovincristine | 1.8 | 1.5 |
| 5′-noranhydrovincristine | 0.8 | 0.66 |
| 5′-norleurosine | 1.0 | 3 |
| 5′-nor N$_a$-desmethyl N$_a$-formyl leurosine | 2.77 | 2.5 |

(a) I$_{50}$: concentration of the product inhibiting 50% of the velocity of polymerisation of the tubulin. I$_{50}$ vinblastine = 2,10$^{-6}$.
(b) S$_{50}$: concentration of the product required for inducing 50% of the maximum spiralisation of the tubulin.

The relations between the action on tubulin and the anti-tumoral properties are described in particular in the Article by F. Zavala et al in Experientia 34, 1497 (1978).

The product of Example 1 does not have any "spiralising" activity although it does have activity similar to vinblastine in regard to the inhibition of polymerisation.

(2) Activity in the P388 leukaemia test on mice

Table II below exemplifies the results obtained with the compound of Example 1 in the form of its tartrate in the treatment of P388 leukaemia.

TABLE II

| | Physiological serum (control) | 5 mg/kg | 10 mg/kg | 25 mg/kg |
|---|---|---|---|---|
| Number of mice | 10 | 10 | 10 | 10 |
| Mean survival period (days) | 10.5 ± 0.8 | 13.6 ± 0.8 | 17.9 ± 0.9 | ≧ 24.3 |
| I.L.S. $v = \frac{T-C}{C} \times 100$ | | 29.5 | 70.5 | ≧ 131.4 |
| $a = \frac{T}{C} \times 100$ | | 129.5 | 170.5 | ≧ 231.4 |

T=average life (in days) of the mice of the treated group
C=average life (in days) of the mice of the control group
Mice: DBA/2 ♀
Graft: P 388 (10$^6$ cell./mice ip)
Treatment: i.p.
Graft→treatment interval: 24 h.

(3) Activity in the L1210 leukaemia test on mice

Table III below summarises the results obtained with the compound of Example 1 in the form of its tartrate in the treatment of L1210 leukaemia:

TABLE III

| | Physiological serum (control) | 5 mg/kg | 10 mg/kg | 25 mg/kg |
|---|---|---|---|---|
| Number of mice | 10 | 10 | 10 | 10 |
| Mean survival period (days) | 8.6 ± 0.4<br>8.6 ± 0.7 | 12.0 ± 0.9 | 13.5 ± 0.9<br>12.9 ± 1.3 | 14.2<br>±0.7<br>13.5<br>±0.7 |
| I.L.S. | | | 57 | 65 |

TABLE III-continued

|  | Physiological serum (control) | 5 mg/kg | 10 mg/kg | 25 mg/kg |
|---|---|---|---|---|
| $\frac{T-C}{C} \times 100$ |  | 40 | 50 | 57 |
| $\frac{T}{C} \times 100$ |  | 140 | 157<br>150 | 165<br>157 |

Mice: DBA/2 ♀
Graft: L1210
Treatment: i.p.
Graft→treatment interval: 24 h.
Conc. 0.5 and 1 mg/ml in physiological serum.

(4) Toxicity of the product of Example 1 in tartrate form

A single dose of the test product is intraperitoneally administered to DBA/2 ♀ mice and the mortality rate studied over a period of 35 days. The following results are obtained:

TABLE IV

| Dose (mg/kg) | Number of mice | Distribution of mortality | | | | | Mortality over 35 days |
|---|---|---|---|---|---|---|---|
|  |  | 1 | 3 | 4 | 6 | 9 |  |
| 25 | 5 |  |  |  |  |  | 0 |
| 50 | 5 |  | 1 | 1 | 1 | 1 | 4/5 |
| 75 | 5 | 3 | 1 |  | 1 |  | 5/3 |
| 100 | 3 |  | 3 |  |  |  | 3/3 |

A $DL_0$ of 25 mg/kg is thus observed, being comparable with a
$DL_{10}=3$ mg/kg for vincristine,
$DL_{50}=2$ mg/kg for vincristine (i.v.)
$DL_{50}=17$ mg/kg for vinblastine (i.v.)

All these tests show that the compound of Example 1 is more active than vincristine and vinblastine on the leukaemia studied and far less toxic.

The present invention also relates to the pharmaceutical compositions containing a new compound corresponding to general formula (I) or one of its salts, optionally in association with other compatible inert or physiologically active pharmaceutical products.

These compositions may be made up in various forms suited to the method of administration envisaged. The parenteral route is the preferred route of administration, particularly the intravenous route.

The compositions according to the present invention for parenteral administration may be aqueous or non-aqueous sterile solutions, suspensions or emulsions. The solvent or vehicle used may be propylene glycol, polyethylene glycol, vegetable oils, particularly olive oil or injectable organic esters, particularly ethyl oleate. These compositions may also contain additives, particularly wetting agents, emulsifiers and dispersants. Sterilisation may be obtained in several ways, for example by means of a bacteriological filter, by incorporating sterilising agents in the composition, by irradiation or by heating. They may also be prepared in the form of sterile solid compositions which may be dissolved or dispersed at the amount of use either in water or in other sterile injectable media.

The new compounds or salts thereof are active in the treatment of solid or liquid tumors, more particularly human cancers, in daily doses of from 10 to 20 mg for adults, The following Example illustrates a particular composition according to the present invention:

EXAMPLE

A solution containing 10 mg/cc of active material is prepared by dissolving 1 g of the product I' of the Example in 100 cc of apyrogenic physiological aqueous solution. The solution obtained is introduced under aseptic conditions into 2 cc ampoules in a quantity of 1 cc per ampoule. The ampoules are sealed and each contain 10 mg of active principle.

What is claimed is:

1. Compounds corresponding to the following formula (I):

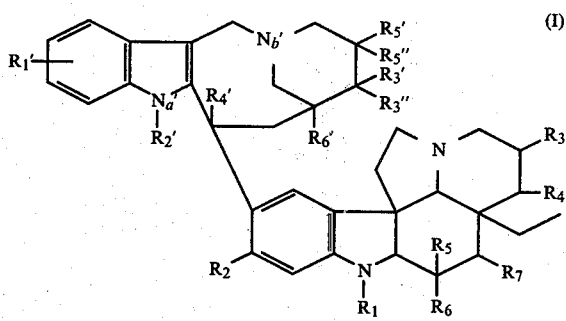

wherein
$R'_1$ is selected from the group consisting of a hydrogen atom and an alkoxy, acyl, formyl and haloacyl radical, said alkoxy radical containing from 1 to 5 carbon atoms, said acyl and haloacyl radical containing from 2 to 5 carbon atoms;
$R'_2$ is selected from the group consisting of a hydrogen atom and an alkyl radical, said alkyl radical containing from 1 to 5 carbon atoms;
$R'_3$ and $R''_3$ are independently selected from the group consisting of a hydrogen atom and a hydroxyl radical and an alkanoyloxy radical, said alkanoyloxy radical containing from 2 to 5 carbon atoms, and together are an oxo group, and $R'_3$ and $R'_5$ together are an epoxy bridge or a double bond;
$R'_4$ is selected from the group consisting of a hydrogen atom and an alkyloxycarbonyl, hydroxymethyl, alkanoyloxymethyl and acetamido radical;
$R'_5$ and $R''_5$ are independently selected from the group consisting of a hydrogen atom and a hydroxyl, alkanoyloxyl, ethyl and 2-hydroxyethyl radical, said alkanoyxloxyl radical having from 2 to 5 carbon atoms;
$R'_6$ is selected from the group consisting of a hydrogen atom and an ethyl, 2-hydroxyethyl and acetyl radical;
$R_1$ is selected from the group consisting of a hydrogen atom and an alkyl, formyl and acyl radical, said alkyl radical having from 1 to 5 carbon atoms, said acyl radical having from 2 to 5 carbon atoms;
$R_2$ is selected from the group consisting of a hydrogen atom and alkoxy radical, said alkoxy radical containing from 1 to 5 carbon atoms;
$R_3$ is selected from the group consisting of a hydrogen atom and a hydroxyl and alkanoyloxyl radical, said alkanoyloxyl radical containing from 2 to 5 carbon atoms, and together with $R_4$ is selected from the group consisting of an epoxy bridge and a double bond;

$R_4$ is selected from the group consisting of a hydrogen atom and a hydroxyl, alkanoyloxyl radical of from 2 to 5 carbon atoms, and together with $R_5$ is an epoxy bridge;

$R_6$ is selected from the group consisting of an alkyloxycarbonyl, hydrazido, acetamido, hydroxymethyl and alkanoyloxymethyl radical; and $R_5$ and $R_7$ are selected from the group consisting of a hydrogen atom and a hydroxyl and alkanoyloxyl radical of from 2 to 5 carbon atoms;

acid addition and quaternary ammonium salts thereof and 12-chloro derivative thereof.

2. Compounds corresponding to claim 1 corresponding to the following formula (Ia):

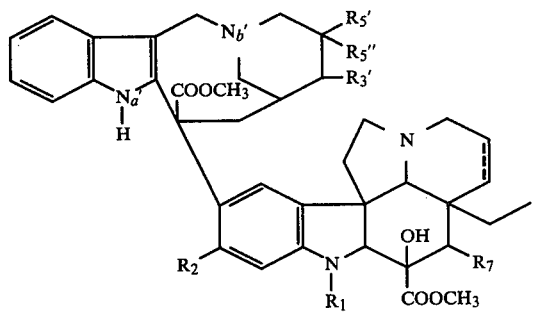

(Ia)

wherein
$R'_3$ is selected from the group consisting of a hydrogen atom and a hydroxy radical;
$R'_5$ is selected from the group consisting of a hydrogen atom and a hydroxy radical;
$R'_3$ and $R'_5$ are together selected from the group consisting of an epoxy bridge and a double bond;
$R''_5$ is selected from the group consisting of a hydrogen atom and an ethyl radical;
$R_1$ is selected from the group consisting of a hydrogen atom, an alkyl, formyl and acyl radical, said alkyl radical having 1 to 5 carbon atoms, said acyl radical having from 2 to 5 carbon atoms;
$R_2$ is selected from the group consisting of a hydrogen atom and a methoxy radical;
$R_7$ is an alkanoyloxyl radical of from 2 to 5 carbon atoms; (the dotted line represents a possible double bond); and the corresponding salts thereof.

3. Compounds selected from the group consisting of
5'-noranhydrovinblastine,
5'-noranhydrovincristine,
5'-norleurosine,
12-chloro-5'-noranhydrovinblastine, and
5'-nor-$N_a$-desmethyl-$N_a$-formyl leurosine.

4. Pharmaceutical compositions for the treatment of leukemia comprising an effective amount of at least one compound according to claim 1.

5. Method of treating leukemia comprising administering an effective amount of at least one compound according to claim 1.

6. Compounds corresponding to formula (IV):

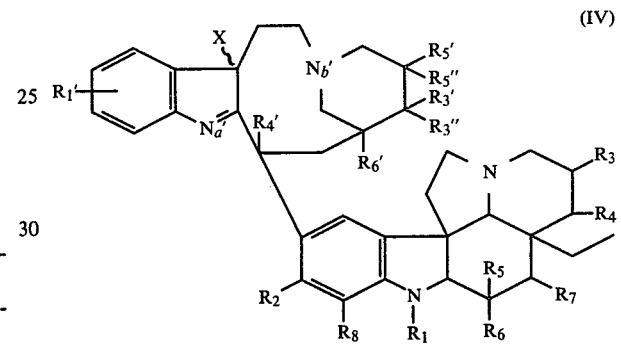

(IV)

wherein the radicals are as defined in connection with formula (I); and
X represents a halogen atom and $R_8$ represents a halogen atom.

* * * * *

UNITED STATES PATENT AND TRADEMARK OFFICE

CERTIFICATE EXTENDING PATENT TERM
UNDER 35 U.S.C. § 156

PATENT NO.    :  4,307,100

ISSUED        :  December 22, 1981

INVENTOR(S)   :  Nicole Langlois et al.

PATENT OWNER  :  Centre National de la Recherche Scientifique (C.N.R.S.)

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,053 days from the date of expiration of the original patent term, August 20, 1999, with all rights pertaining thereto as provided by 35 U.S.C. § 156(b).

I have caused the seal of the Patent and Trademark Office to be affixed this 23rd day of September 1996.

Bruce A. Lehman
Assistant Secretary of Commerce and
Commissioner of Patents and Trademarks